US00PP25763P3

(12) United States Plant Patent
Firoozbady et al.

(10) Patent No.: US PP25,763 P3
(45) Date of Patent: Aug. 4, 2015

(54) PINEAPPLE PLANT NAMED 'ROSÉ'

(50) Latin Name: *Ananas comosus*
Varietal Denomination: Rosé

(75) Inventors: Ebrahim Firoozbady, Coral Gables, FL (US); Thomas R Young, Coral Gables, FL (US)

(73) Assignee: DEL MONTE FRESH PRODUCE, Coral Gables, FL (US)

( * ) Notice: Subject to any disclaimer, the term of this patent is extended or adjusted under 35 U.S.C. 154(b) by 0 days.

(21) Appl. No.: 13/507,101

(22) Filed: Jun. 4, 2012

(65) Prior Publication Data

US 2013/0326768 P1 Dec. 5, 2013

(51) Int. Cl.
*A01H 5/00* (2006.01)
*A01H 5/08* (2006.01)

(52) U.S. Cl.
USPC ..... Plt./156
CPC ..... *A01H 5/08* (2013.01)

(58) Field of Classification Search
USPC ..... Plt./158, 258, 370
See application file for complete search history.

(56) References Cited

U.S. PATENT DOCUMENTS

| | | | | |
|---|---|---|---|---|
| 7,663,021 | B2 | 2/2010 | Young et al. | |
| PP20,885 | P3 * | 3/2010 | Young et al. | Plt./156 |
| 8,049,067 | B2 | 11/2011 | Firoozabady | |

FOREIGN PATENT DOCUMENTS

| | | | |
|---|---|---|---|
| AU | 2006236392 | | 11/2011 |
| EP | 1874110 | A2 | 1/2008 |
| WO | WO 2006113709 | | 10/2006 |

OTHER PUBLICATIONS

Hirschberg, I, M. Cohen, M. Harker, T. Lota, V Mann, and I. Pecker. 1997. Molecular genetics of carotenoid biosynthesis pathway . . . Pure Appl. Chem. 69:2145-2150.
Ikomaa, Yoshinori, Akira Komatsub, Masayuki Kitac, et al. (2001) Expression of a phytoene synthase gene . . . Physiologia Plantarum 111: 232-238.
Itoh; Y., Watson, J.M., Haas, D., Leisinger, T. (1984) Genetic and molecular characterization of the *Pseudomonas* plasmid pVS1. Plasmid 11:206-220.
Koncz C, and Schell J. (1986) The promoter of TL-DNA gene 5 controls the tissue-specific . . . Mol Gen Genet 204: 383-396.
Neuteboom LW, Kunimitsu WY, Webb D, Christopher DA, 2002. Characterization and tissue-regulated expression of genes involved in pineapple . . . Plant Science, 165:1021-1035.
Turnbull, C.G.N.; Nissen, R.J.; Sinclair, E.R.; . . . Ethephon and causes of flowering failure in pineapple. Acta Horticulturae, Honolulu, n.334, p. 83-88, 1993.
Waters, S. H., Rogowski, P., Ginsted, J., Altenbuchner, J., and Schmidt, R. (1983) The tetracycline resistance determinants of RP1 and . . . Nuc. Acids Res. 11(17):6089-6105.
Lee, K. et al., (1988) The molecular basis for sulfonylurea herbicide resistance in tobacco. EMBO J. 7:1241-1248.
InfoStat-Statistical Software, version 2011, National University of Cordoba, Argentina.
Adams DO, Yang SF. 1979. Ethylene biosynthesis: Identification of 1-aminocyclopropane-1-carboxylic acid as an intermediate in the conversion of methionine to ethylene. Proc.
Barker, R., Idler, K., Thompson, D., Kemp, J. (1983) Nucleotide sequence of the T-DNA region from the *Agrobacterium tumefaciens* octopine Ti plasmid pTi15955. Plant Mol. Bio.
Burg S.P, Burg E.A. 1966. Auxin-induced ethylene formation: its relation to flowering in the pineapple. Science. ;152(3726):1269.
Chaleff, R. S., and Mauvais, C. J. (1984) Acetolactate synthase is the site of action of two sulfonylurea herbicides in higher plants. Science 224:1443-1445.
Chang, A. C. Y. & Cohen, S. N. (1978). Construction and characterisation of amplifiable multicopy DNA cloning vehicles derived from the p15a cryptic miniplasmid. J Bacter.
Cunningham, F.X., Pogson, B.J., Sun, Z., McDonald, K., DellaPenna, D., and Gantt, E. (1996). Functional analysis of the beta and epsilon lycopene cyclase enzymes of Arabi.
Cunningham, F.X., Jr., and Gantt, E. (1998). Genes and enzymes of carotenoid biosynthesis in plants. Annu. Rev. Plant Physiol. Plant Mol. Biol. 49, 557-583.
Eckes, P., Rosahl, S., Schell, J. and Willmitzer, L., (1986) Isolation and characterization of a light-inducible, organ-specific gene from potato and analysis of its expr.
Fraser, P. D., & Bramley, P. M. (2004). The biosynthesis and nutritional uses of carotenoids. Progress in lipid research, 43(3), 228-65.
Hirschberg, J. (2001). Carotenoid biosynthesis in flowering plants. Curr. Opin. Plant Biol. 4, 210-218.

* cited by examiner

*Primary Examiner* — Annette Para
(74) *Attorney, Agent, or Firm* — John Dodds

(57) ABSTRACT

A new pineapple (*Ananas comosus*) variety of the Bromeliaceae family was developed, via genetic engineering of MD2, named 'Rosé' is provided. Internal light red color with yellow spots, unique shell morphology and possibility of flowering control trait are traits of the new variety.

10 Drawing Sheets

Species name: *Ananas comosus.*
Variety denomination: 'Rosé', with breeder name 'EF2-114'.

BACKGROUND OF THE INVENTION

There is a continuous need for production of novel varieties of pineapple with distinct color, higher carotenoid content and flowering tolerance trait.

SUMMARY OF THE INVENTION

A new variety of pineapple (*Ananas comosus*), family Bromeliaceae, has been developed using genetic engineering techniques and named 'Rosé' or international breeder name 'EF2-114'. Using crown materials from variety MD2 (also known as Del Monte Gold pineapple) to produce in vitro shoot cultures, introduce genes and DNA elements into leaf base sections, regenerate complete plants, perform field trials and select plants with internal pink- or red-colored fruits. The selected plants were asexually propagated in the field and via meristem culture to confirm the color and other traits related to fruit and agronomic performance. The invention relates to production of a new and distinct variety of the Bromeliaceae, or pineapple family.

The new plant variety 'Rosé' is characterized by light red flesh color (FIGS. 4 and 6) and "Tiger" shell color, when compared with the parental line, MD2, and it might be tolerant to natural occurrence of flowering. Internal color of fruits can be variable for intensity of the light red color depending on the stage of ripening. The Tiger trait is defined as the color in shell has in the shoulder of each fruitlet a combination of colors green, yellow, orange and red due to expression of carotenoid genes in the shell (FIGS. 5-7). The plant morphology generally is the same as MD2, the parental plant (FIGS. 8-11).

RB—Right Border pVS1—*Agrobacterium* origin of replication

TetR/A—Tetracyclin gene (bacterial selectable marker)

pACYC—Bacterial origin of replication

LB—Left Border

Figure 3:
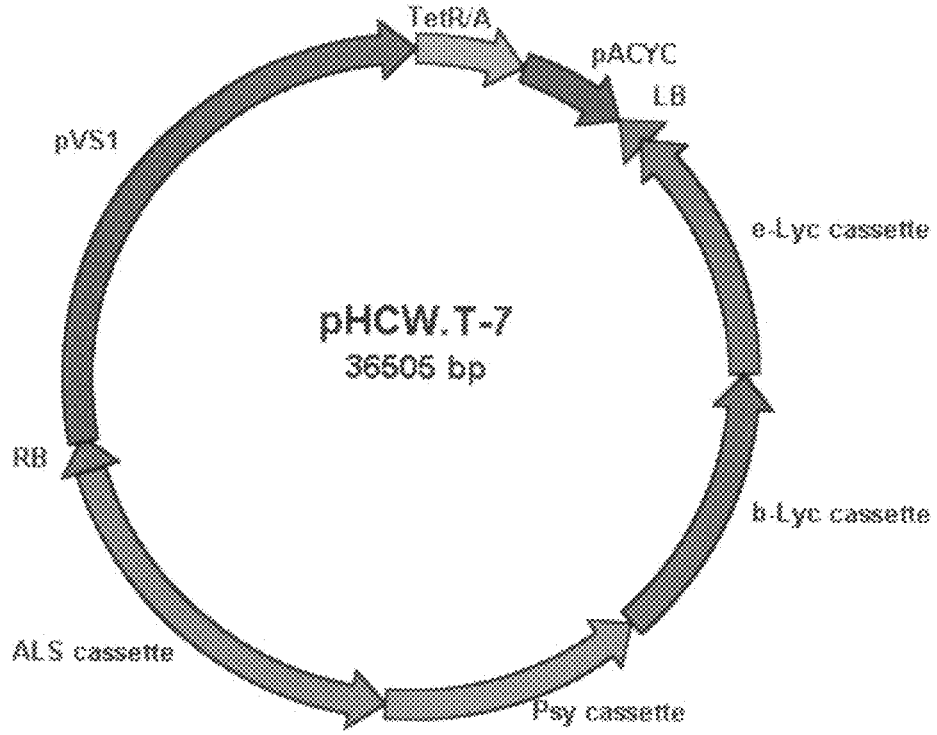
Figure 3:
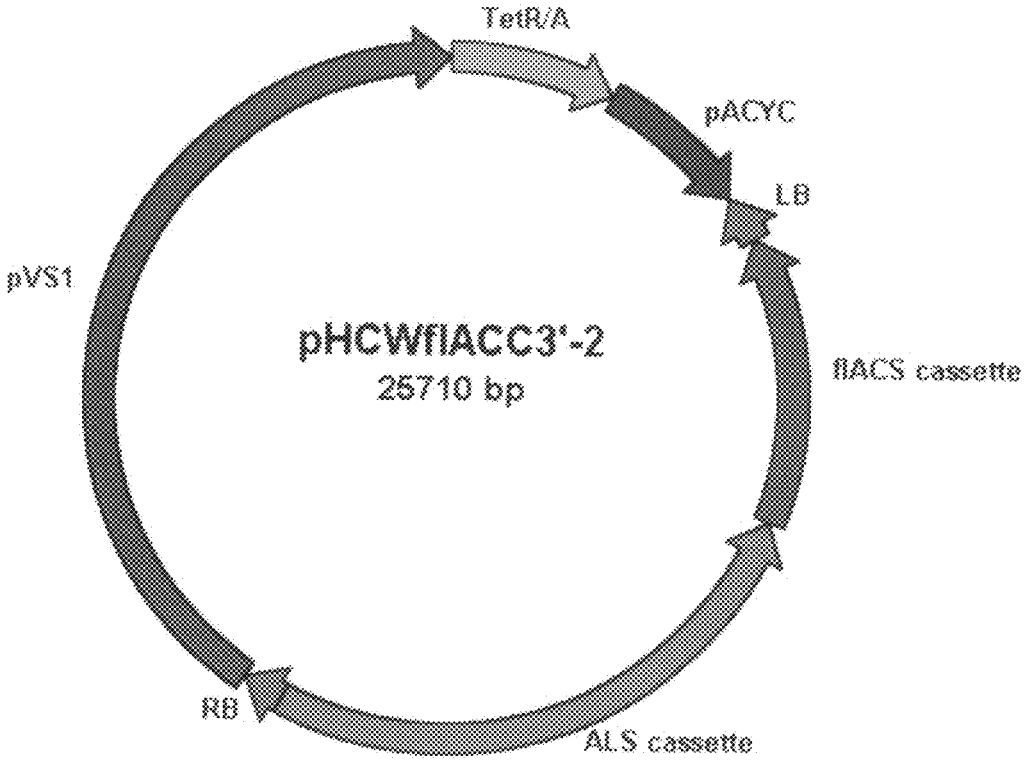

FIG. 3. Plasmid pHCW1 was used to create pHCW.T-7 binary vector (in AG76) and pHCWflACC3'-2 binary vector (in AG62). For definition of genetic elements see Table 2 and 3.

Vector Backbone:

RB: Right T-DNA Border pVS1: *Agrobacterium* origin of replication

TetR/A: Tetracyclin gene (bacterial selectable marker)

pACYC: Bacterial origin of replication

LB: Left T-DNA Border

T-DNA

ALS cassette: EHS-Ubp (promoter)-ALS-ALS3' terminator

Figure 4:
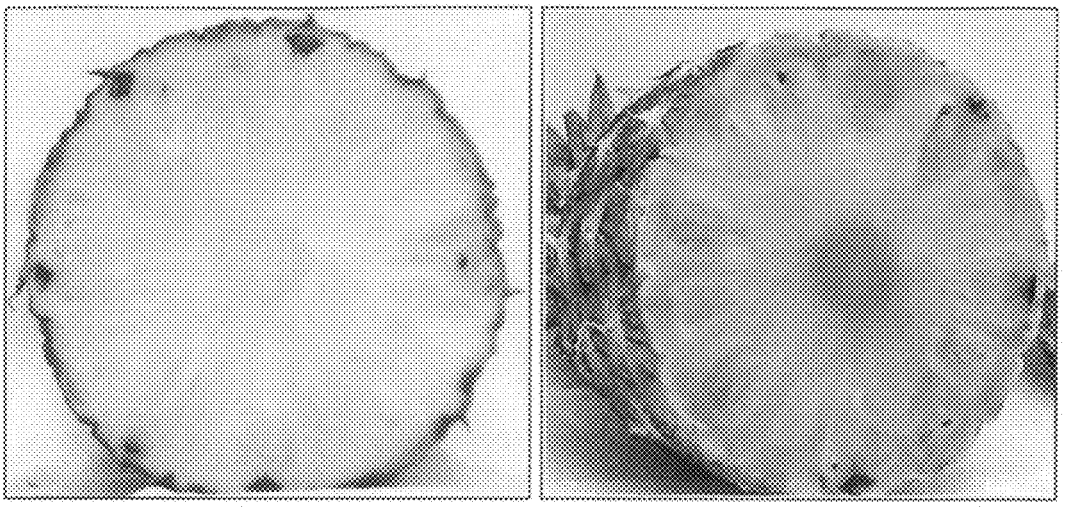

Psy casssette: BRIP (promoter)-Psy-Ubp terminator bLyc cassette: BRIP (promoter)-bLyc(+)-LS1 intron-bLyc(−)-Ubp terminator eLyc cassette: BRIP (promoter)-eLyc(+)-LS1 intron-eLyc(−)-Ubp terminator flACS cassette: Ubp(promoter)-flACS(+)-LS1 intron-flACS(−)-Ubp terminator FIG. 4. Event EF2-114 fruit (right) exhibits light red color in the flesh due to accumulation of lycopene while parental variety MD2 (left) has a golden flesh color.

Figure 5:
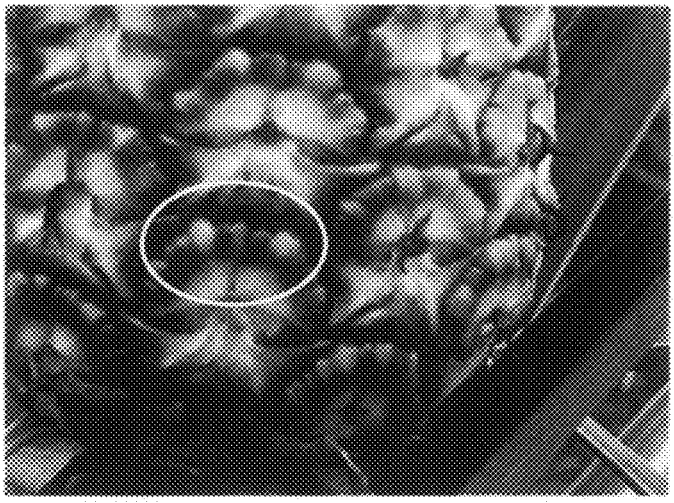
Figure 5:
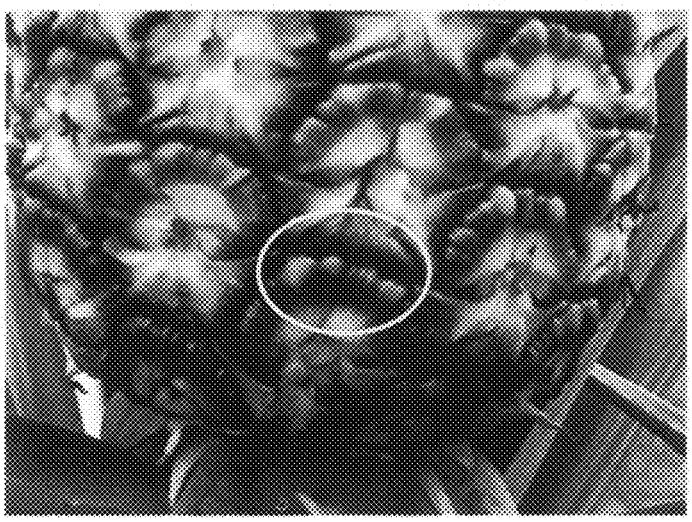

FIG. 5. Shows "Tiger" shell color in 'Rosé' fruits. The color in shell has in the shoulder of each fruitlet a combination of colors green, yellow, orange and red.

Figure 6:
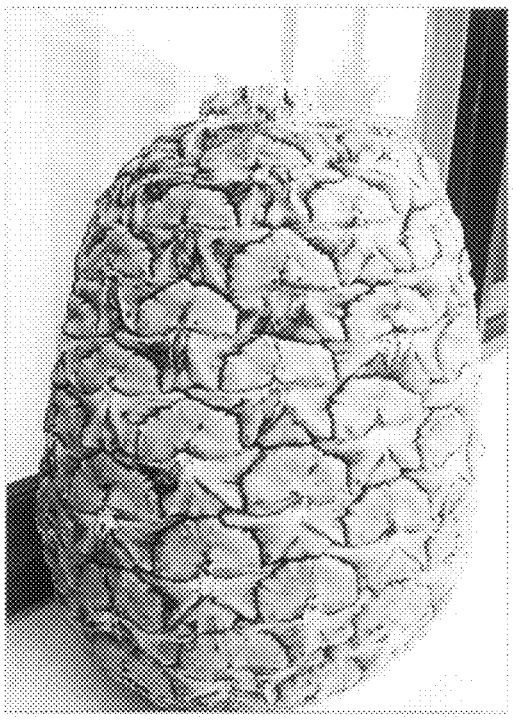
Figure 6:
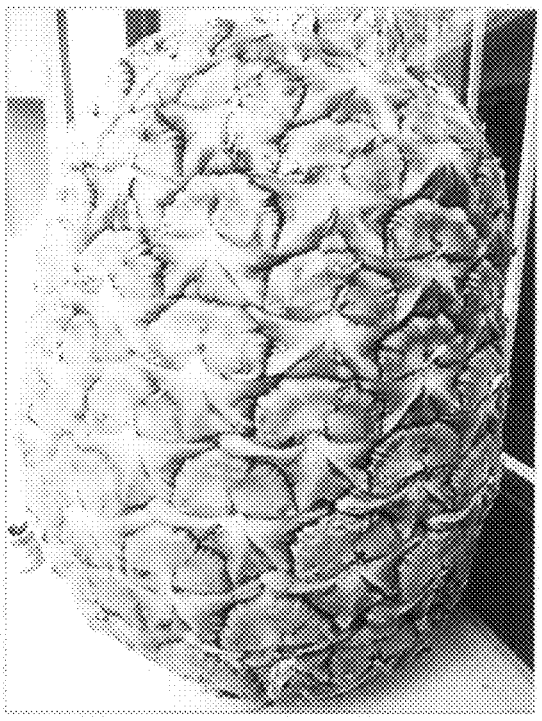
Figure 6:
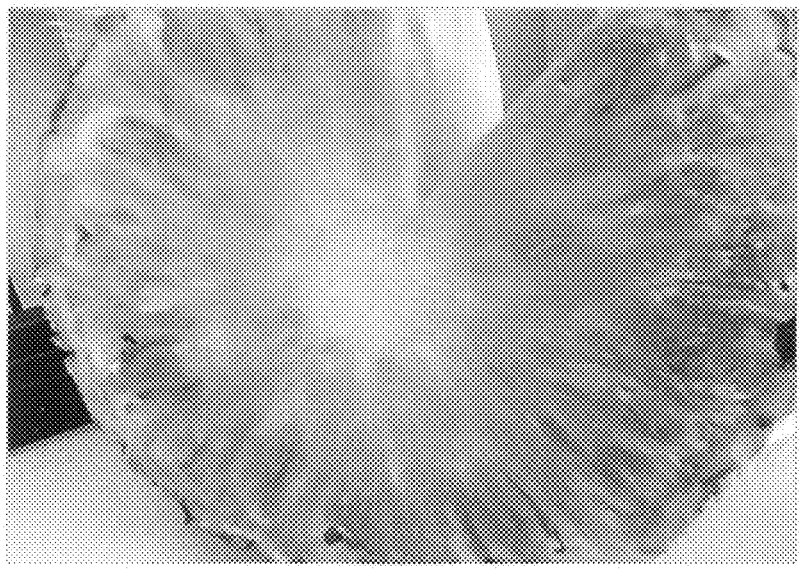

FIG. 6. A "Tiger" fruit showing shell and internal color at harvest.

Figure 7:
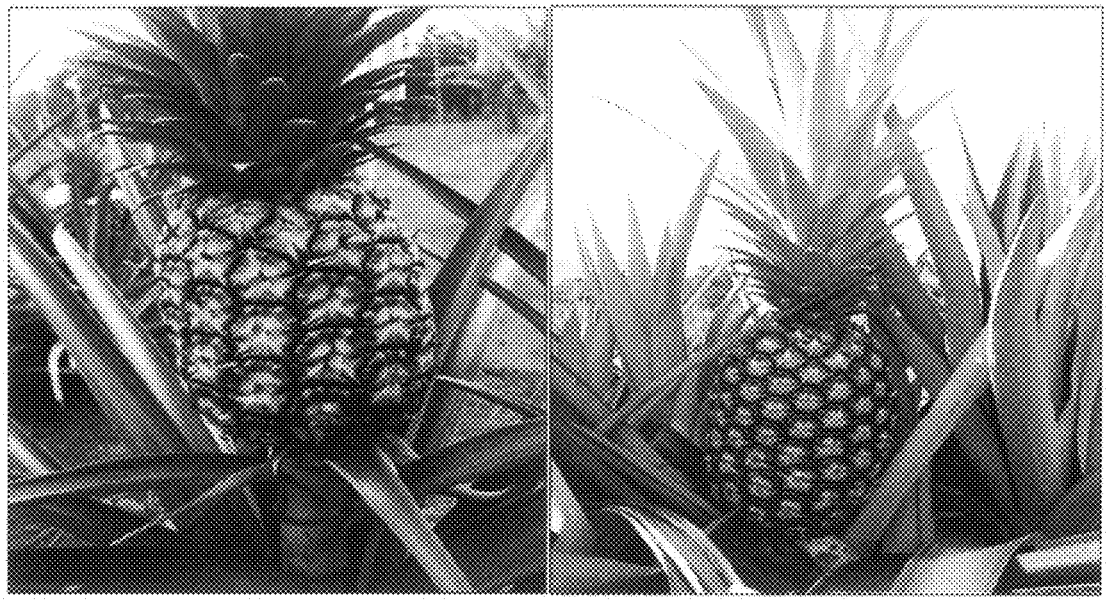

FIG. 7. Shows an immature fruit of 'Rosé' with Tiger shell morphology (left) and an immature fruit of MD2 (right) both ~145 days after forcing.

Figure 8:
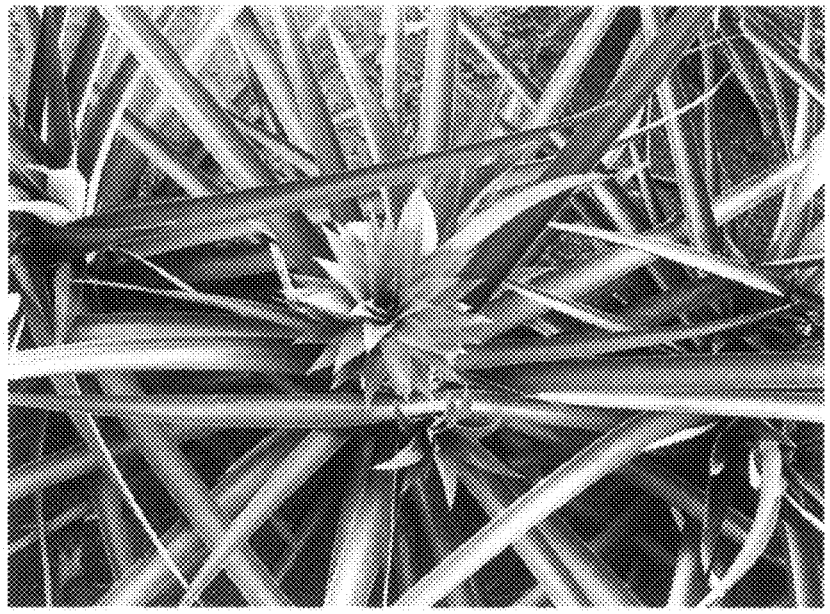

FIG. 8. Shows overhead view of 'Rosé' plant.

Figure 9:
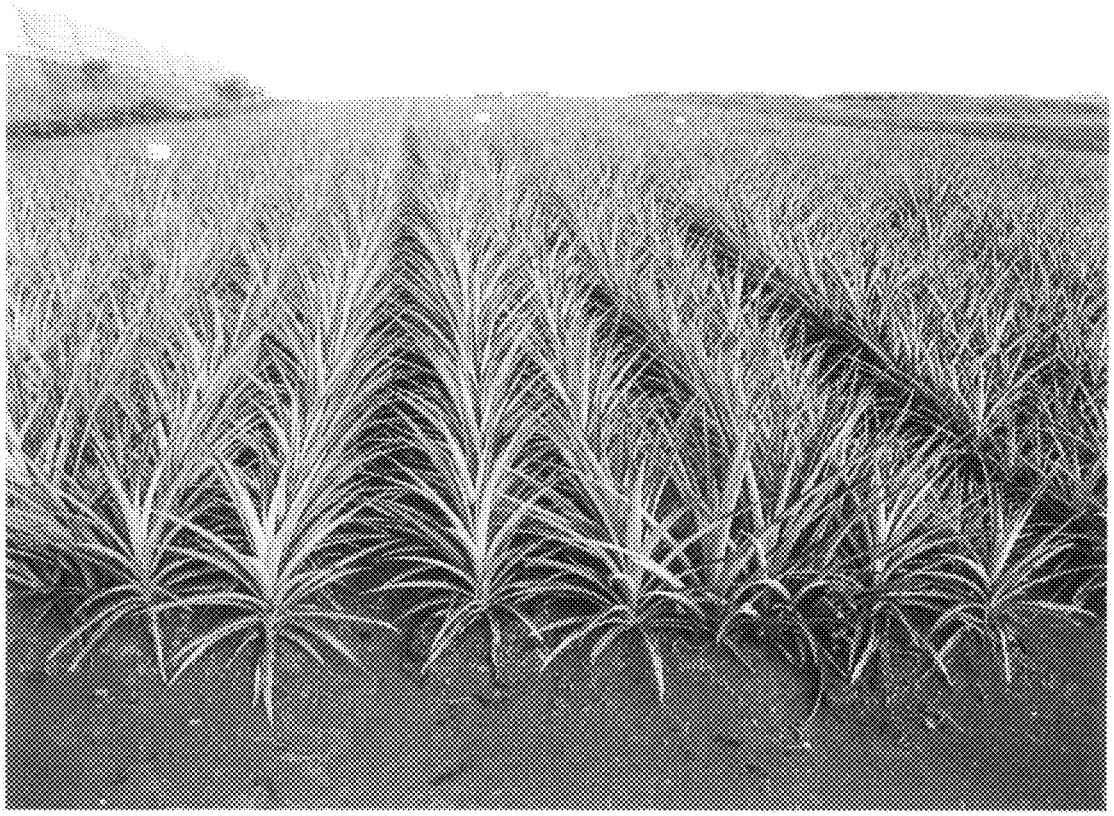

FIG. 9. Shows a 'Rosé' plantation.

Figure 10:
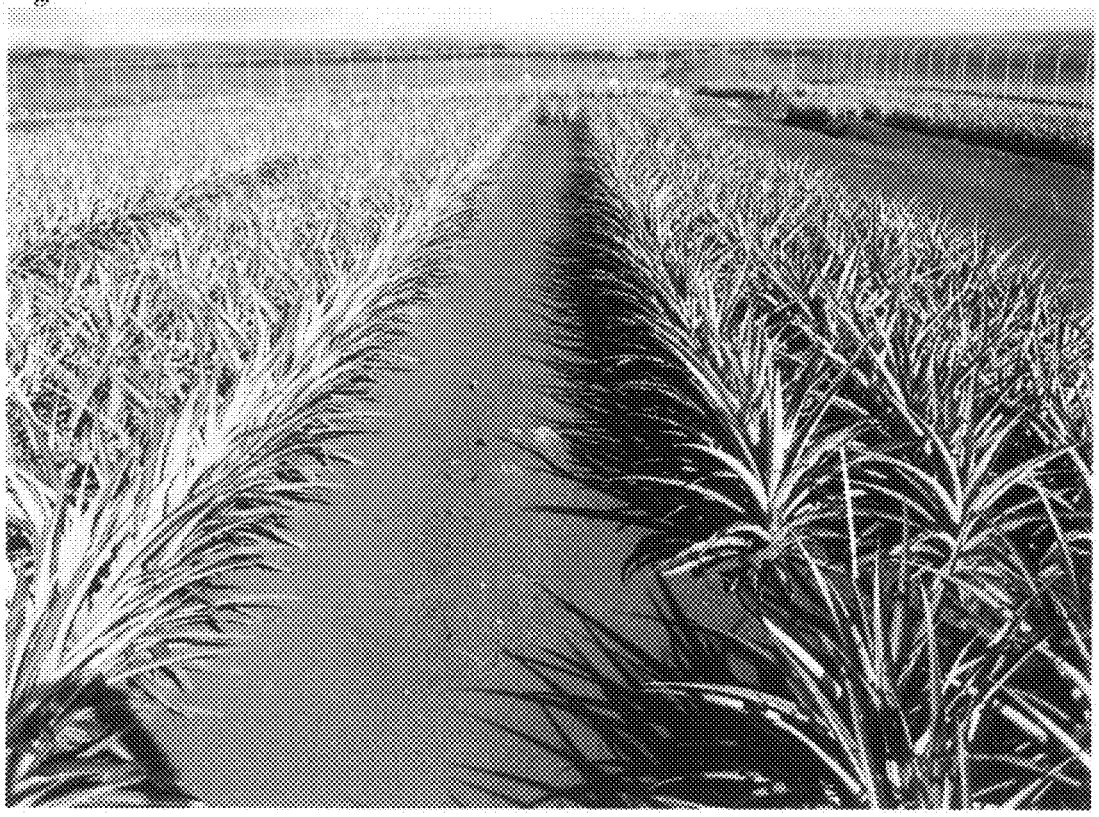

FIG. 10. Shows 'Rosé' (left) and MD2 (right) experimental plots.

Figure 11:
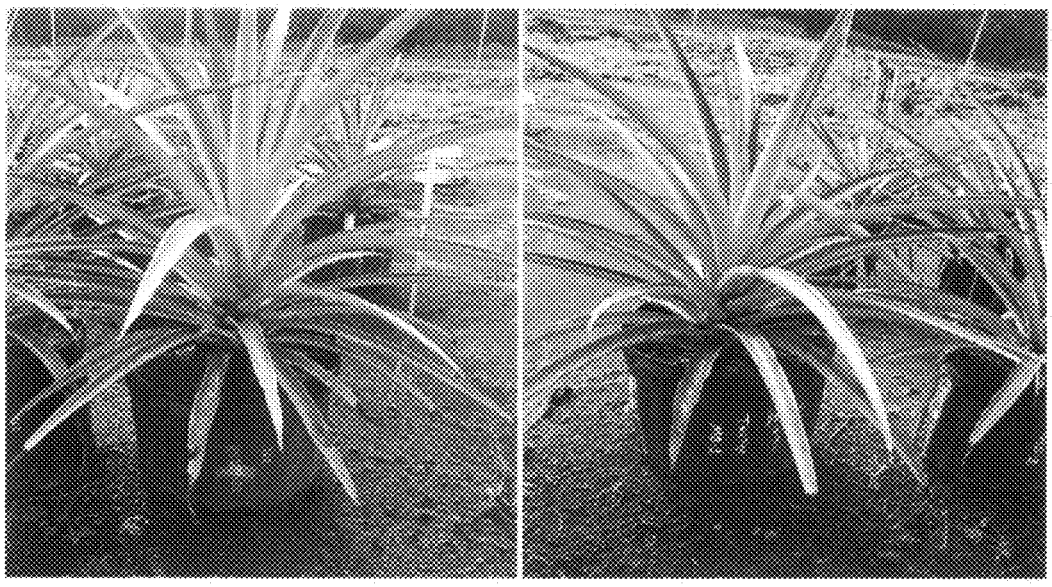

FIG. 11. Shows 'Rosé' (left) and MD2 (right) meristem culture-derived plants. After 15 weeks growth in greenhouse, ~15 cm long plants were transplanted in pots, and the pictures were taken 11 months later.

Figure 12:
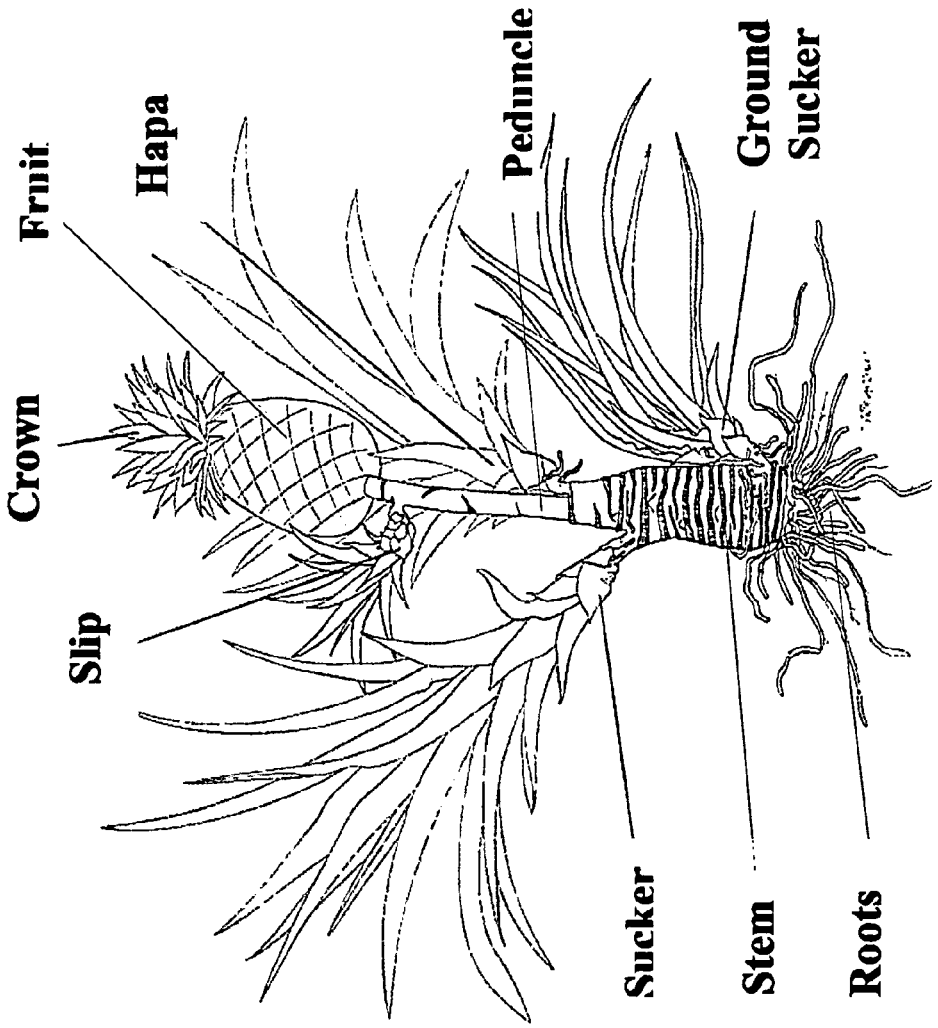

FIG. 12. Pineapple plant morphology.

DETAILED DESCRIPTION OF THE INVENTION

A new variety of pineapple (*Ananas comosus*), family Bromeliaceae, has been developed using genetic engineering techniques and named 'Rosé'. This process took 6 years; started in August 2005, using crown materials from variety MD2 (also known as Del Monte Gold pineapple) that is not patented, imported from Hawaii, to produce in vitro shoot cultures, introduce genes and DNA elements into leaf base sections, regenerate complete plants, perform field trials and select plants with internal pink- or red-colored fruits. The selected plants were asexually propagated in the field and via meristem culture to confirm the colored traits and other traits related to fruit and agronomic performance. Testing and selection of four consecutive asexual generations took place from 2010 through 2014, in Costa Rica-Central America. During the field trials six groups of plants exhibited light red internal color. Molecular analyses confirmed that all of the groups are one transgenic event and collectively are referred as 'Rosé' pineapple variety. The new variety transmits the new traits from one generation to the next through asexual propagation using different propagules including use of ratoon, slips, ground sucker, hapa, stem sectioning and crown.

The 'Rosé' plant is very similar to parental line, MD2, for plant and fruit characteristics and fruit internal quality. However, in 'Rosé' the internal flesh color is light red with yellow spots, due to accumulation of lycopene in the edible part of fruit, the shell morphology is unique and referred as "Tiger" and it might be tolerant to natural occurrence of flowering. The tolerance to natural flowering has not yet been demonstrated for 'Rosé'. On the other hand, the parental variety, MD2, produces fruits with yellow flesh color only, does not produce the shell morphology "Tiger" and is sensitive to natural flowering.

The new variety 'Rosé' is best suited for the fresh market and residual fruit may be processed as juice or frozen product. The residual fruits are those not qualified for export (import to the USA). These fruits have cosmetic bruises or damages, or their crowns are deformed.

The main objective of this invention was to produce a unique and differentiated variety of pineapple by accumulation of high levels of carotenoids, in particular lycopene that produces red internal color while retaining most of the characteristics of the parental line, MD2. Essentially, carotenoid genes and flowering control gene were added to parental variety MD2 to produce 'Rosé' pineapple variety, which has novel traits such as light red flesh, new shell morphology and maybe flowering control trait.

The invention relates to carotenoid biosynthesis in pineapple plants. More specifically, this novel pineapple was produced by genetically transforming MD2 cells in tissue culture and regenerating complete plants. Transformation was accomplished with expression regulators that modulate lycopene biosynthesis in the internal section of the fruit as well as genes involved in ethylene biosynthesis pathway to control flowering in the plants.

Carotenoids are isoprenoid molecules that are widespread in nature and can occur as pigments in fruits, flowers, birds, and crustaceans. Animals are unable to synthesize carotenoids de novo, and rely upon the diet as a source of these compounds. Carotenoids may contribute fundamentally to human health and in recent years there has been considerable interest in dietary carotenoids with respect to their potential in alleviating age-related diseases in humans. This attention has been mirrored by significant advances in cloning most of the carotenoid genes and in the genetic manipulation of crop plants with the intention of increasing levels in the diet.

Figure 1:
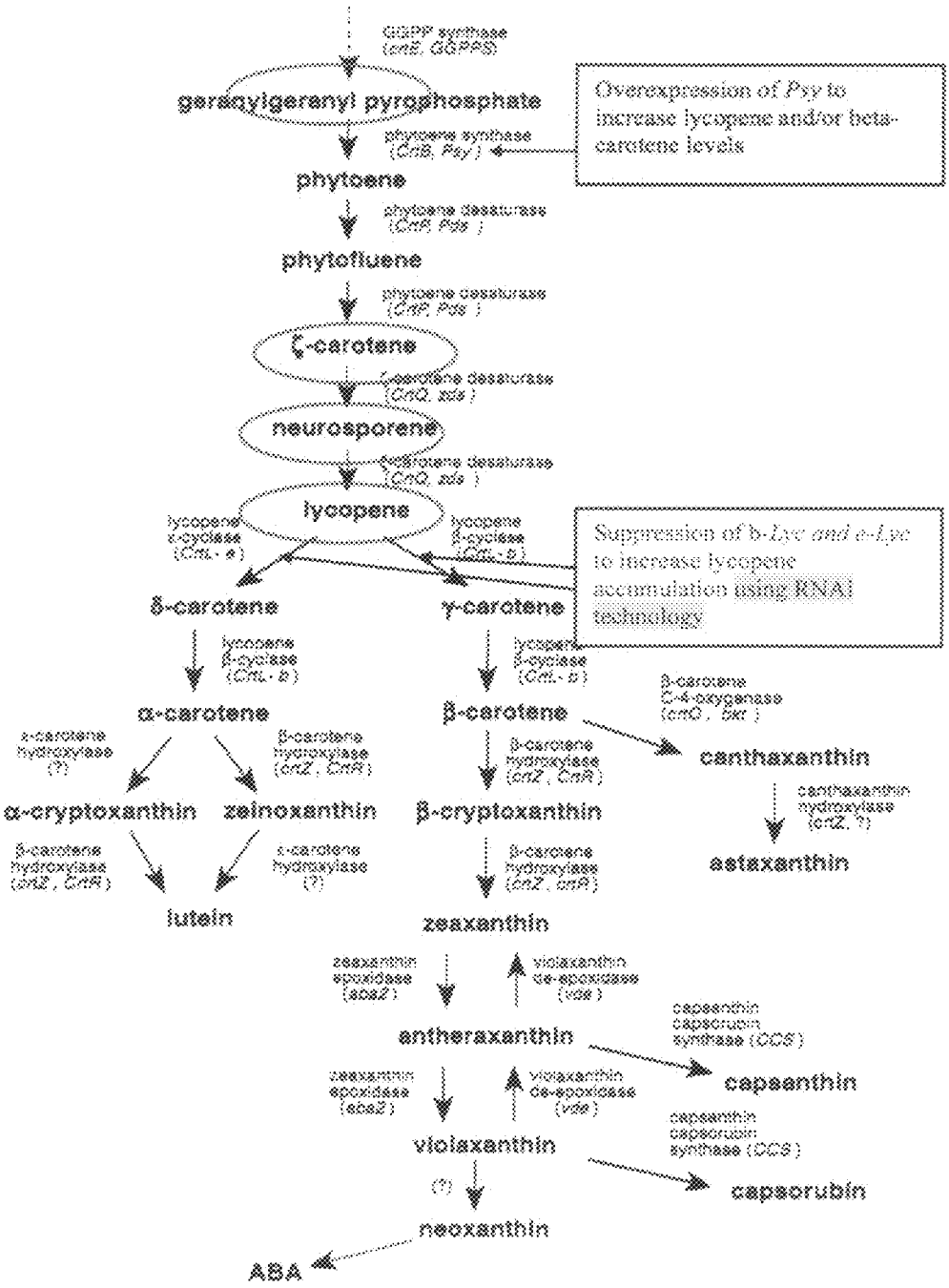
FIG. 1. Enzymes and genes in the carotenoid biosynthesis pathway in plants and algae. (Adapted from J. Hirschberg et al., Pure & Appl. Chem. 69(10):2151-58). Genes used in pineapple transformations to create 'Rosé' are shown in the boxes. Psy is phytoene synthase gene from tangerine and b-lyc and e-Lyc are partial sequences of pineapple lycopene β-cyclase and lycopene ϵ-cyclase genes respectively.

In plants, carotenoids are essential components of the photosynthetic apparatus and are responsible for the red, orange, and yellow color of many flowers and fruit. Our understanding of carotenoid biosynthesis has advanced dramatically in recent years (Hirschberg, 2001; Fraser and Bramley, 2004). The pathway involves a series of desaturations, cyclizations, hydroxylations, and epoxidations commencing with the formulation of phytoene (See FIG. 1). A subsequent series of desaturations is responsible for lycopene synthesis. After the desaturation reactions, the cyclization of lycopene is catalyzed by two enzymes, the beta-cyclase and the zeta-cyclase, leading to the formation of beta-carotene (two beta-rings) and alpha-carotene (one beta-ring and one zeta-ring) (Cunnigham et al., 1996, 1998).

The genes of interest are derived from edible plant species, pineapple (*Ananas comosus*) or tangerine (*Citrus unshiu*). Specifically, a tangerine phytoene synthase gene (Psy) (Ikoma et al, 2001) is under transcriptional control of the pineapple bromelain inhibitor (BRI) gene. We have also suppressed endogenous lycopene β-cyclase (b-Lyc) and/or lycopene ϵ-cyclase (e-Lyc) gene expression using RNA interference (RNAi) technology in order to increase accumulation of lycopene in edible tissues of pineapple fruit (Young and Firoozabady 2010, U.S. Pat. No. 7,663,021). We constructed sense- and antisense-oriented sequences of the b-Lyc and e-Lyc genes derived from pineapple, which are separated by an intron of the light-inducible tissue-specific LS1 gene derived from potato (*Solanum tuberosum*) to form a hairpin structure. These genes are under transcriptional control of the Bromelain inhibitor gene promoter, which drives strong fruit-enhanced expression of the RNAi construct (Firoozabady, E. and Wintz, H-C 2005 and Wintz H-C and Firoozabady, E. 2011).

Flower initiation in pineapple can occur naturally primarily due to cool temperatures and short days. Natural flowering of pineapple plants is a major industry problem. To achieve the controlled flowering trait, we have altered expression of genes involved in ethylene biosynthesis. Ethylene is a plant hormone that plays an important role in every phase of plant development, including seed germination, fruit ripening, leaf and flower senescence, and abscission. In plants, ethylene is synthesized from the amino acid, Methionine. The immediate precursor of ethylene in higher plants is 1-aminocyclopropane-1 carboxylic acid (ACC) (Adams and Yang, 1979).

Ethylene is known to inhibit flowering in most plants. In mango and pineapple, ethylene promotes flowering (Burg S.P and Burg E.A. 1966). Ethylene, ethylene producing compounds and auxins have been used to induce flowering in commercial pineapple production (Turnbull et al., 1993).

We isolated a meristem-specific ACC synthase (flACCS) gene from pineapple and constructed sense- and antisense oriented sequences of the ACC synthase gene, which are separated by an intron of the light-inducible tissue-specific LS1 gene derived from potato (*Solanum tuberosum*) to form a hairpin structure for RNAi suppression of endogenous ACC synthase. The RNAi construct is under transcriptional control of the meristem-specific ACC promoter derived from pineapple.

Transformation method

Pineapple was transformed by *Agrobacterium tumefaciens*-mediated transformation of organogenic tissues using a method described by Firoozabady (Firoozabady, 2011 U.S. Pat. No. 8,049,067). To achieve both high-carotenoid and controlled flowering phenotypes, *Agrobacterium* strains containing either a transformation plasmid for increased carotenoid biosynthesis (accumulation) or for decreased ethylene biosynthesis were co-cultivated with recipient pineapple tissues. Putative transformed tissues were selected on media containing chlorsulfuron and subsequently screened for the presence of target genes by PCR.

Figure 2:
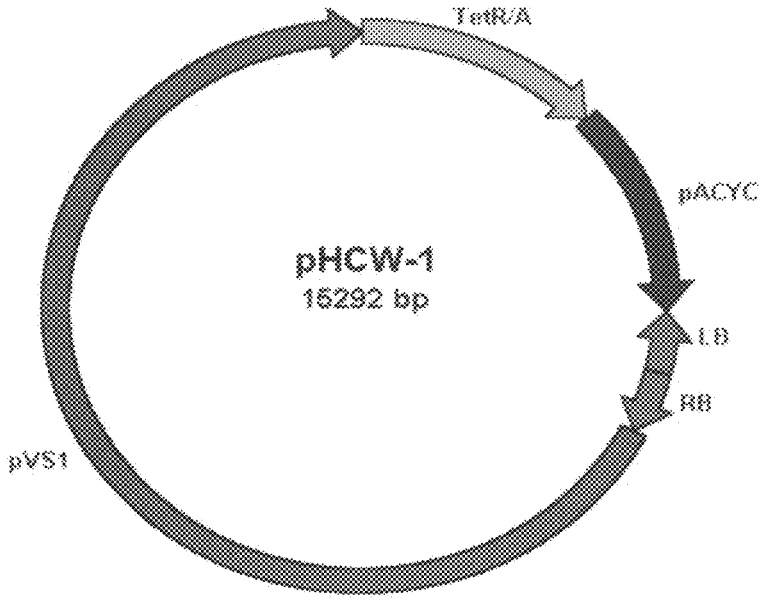
FIG. 2. Map of plasmid binary vector backbone, pHCW1, used for genetic engineering of pineapple. For definition of genetic elements see Table 1.

*A. tumefaciens*, [Strain GV3101] (Koncz and Schell, 1986), is a disarmed *Agrobacterium* strain commonly used for the delivery of T-DNA into plant cells. Different genes were inserted into T-DNA in a binary vector (see FIG. 2) for introduction to pineapple. The Psy derived from *Citrus unshiu*, tangerine (Ikomaa et al, 2001), encodes an enzyme that converts geranylgeranyl pyrophosphate (GGPP) to cis-phytoene, an intermediate in lycopene and beta-carotene biosynthesis.

The lycopene beta-cyclase gene (b-Lyc) derived from *Ananas comosus*, pineapple, encodes an enzyme that converts lycopene to gamma-carotene, a metabolic precursor of beta-carotene.

The lycopene epsilon-cyclase gene (e-Lyc) derived from *Ananas comosus*, pineapple, encodes an enzyme that converts lycopene to sigma-carotene, a metabolic precursor of alpha-carotene.

The modified acetolactate synthase (Chaleff, R. S., and Mauvais, C. J., 1984) (ALS) gene (surBHra) derived from *Nicotiana tabacum*, tobacco, catalyzes the biosynthesis of branched chain amino acids even in the presence of chlorsulfuron (Lee, K. et al., 1988), which allows for the selection of transformed pineapple cells.

Plasmid pHCW1 used for pineapple transformations was constructed by the laboratory of Del Monte Fresh Produce Company, Richmond, Calif. pHCW1 contains a tetracycline resistance gene (tetRA) from plasmid RP1 and the origin of replication from plasmid pACYC, which allows for selection and maintenance in *Escherichia coli* and the pVS1 replicon derived from *Pseudomonas aeruginosa*, which ensures replication in *Agrobacterium tumefaciens*. pHCW1 contains the 25-base pair sequences that delimit the T-DNA transfer and a 110-base pair synthetic sequence between the borders that forms multiple cloning restriction sites to allow integration of different T-DNA cassettes (see Table 1).

The plasmid pCHW1 was used to create pHCW.T-7 and pHCWflACC3'-2 binary vector plasmids. Binary vectors were transferred to disarmed *A. tumefaciens* strain GV3101. The GV3101 with pHCW.T-7 vector was named AG76 and the one with pHCWflACC3'-2 was named AG62 (see FIG. 3).

AG76 and AG62 were mixed together and used for pineapple transformation. Genetic elements of the vectors are described in Tables 2 and 3.

Genetic engineering of the MD2 took place in the Laboratory of Del Monte Fresh Produce Company in Richmond, Calif., USA, where transgenic plants were produced and propagated in tissue culture. Then the propaguls were taken to the research area of Corporacion de Desarrollo Agricola Del Monte, S.A. (Pindeco), Buenos Aires-Puntarenas, Costa Rica, for field evaluation, propagation in the field and in the laboratory for mass propagation of the variety.

BOTANICAL DESCRIPTION OF THE PLANT

The description of the new variety is based on observations of well fertilized specimens which were grown under field conditions, in the Buenos Aires region, Costa Rica (9 degrees and 9 minutes latitude North, and 83 degrees and 20 minutes longitude west, 379 meters above the sea level), where temperatures generally range from 14° C. to 37° C., and annual rainfall averages 3251 mm.

The plants were grown at a research facility in Buenos Aires-Puntarenas, Costa Rica (Pindeco). Essentially, 'Rosé' is same as MD2 for all fruit and plant characteristics with the exception of fruit internal color, Tiger trait and possibly flowering control trait (Tables 4-10). The Munsell Color Chart was used for all color designations ("Munsell Book of Color" Gretag Macneth LLC, 617 Little Britain Road, New Windsor, N.Y. 12553-6148).

Name: *Ananas comosus* (L.) Merr. Var. 'Rosé', family Bromeliaceae, subclass Monocotyledons.

Parentage: 'MD2' or 'Del Monte Gold'.

Origin: Genetic engineering of MD2 followed by selection in the field trials for the traits of interest.

Classification:

*I. Botanic.*—Bromeliaceae or pineapple family. Subfamily: Bromelioideae. Genus: *Ananas*. Subgenus: *comosus*. Variety: 'Rosé', breeder name 'EF2-114'.

*II. Commercial.*—Bromeliad fruit plant.

General form: 'Rosé' grows at a rate of 1.72±0.02 mm per day (Table 7) until it reaches the anthesis stage, when the plant changes from vegetative growth to reproductive stage. This transition involves the formation of the flower meristem. Plant attitude is open, the plant height just before anthesis is 116.0±1.0 cm with a stem height of 34.7±0.5 cm and a D-leaf length of 97.6±2.0 cm (Table 7). Foliage attitude consists of a compact rosette of overlapping sessile leaves arising from a central stem and surrounding a composite inflorescence prior to anthesis. Production of off shoots (suckers, hapas and slips) is very limited, but depending on season slips may vary from 0 to 2.0±1 per plant.

Stems: Stem is upright, covered by overlapping leaves arranged in acropetal fashion and is 34.7±0.45 cm in length (Table 7). The stem color is grayish (7.5GY 7/1).

Leaves: Leaves are sessile, lanceolate in form, elongated and succulent, with acuminate apex shape, forming a rosette with a 5/13 phyllotaxy. They are dark green (5GY 5/6 to 5/10) on the upper surface and light green (5GY 7/4 to 7/10) on the lower surface, with width at mid-leaf of 6-7 cm, spines only in tips (apex), with no anthocyanins accumulation and no variegation. Trichomes are present in the abaxial side of the leaves. Depending on growing conditions, the number of active leaves per plant may vary from 40 to 60.

Inflorescence: In 'Rosé', the number of days from the flower induction to the emergence of the cone (floral bud) is 35±1 days, and 19±1 additional days to the opening of the first flower. The number of days from first to last flower is 14±0.4 days. It produces a total of 91±1 flowers (Table 7). 'Rosé' inflorescence, just like MD2, is composite flowers, with self-incompatible individual bi-sexual flowers containing three sepals, three petals, six stamens, three stigmas, and three pistils (carpels). Disposition of anthers are grouped. Sepals are purple smooth (10P 3/4 to 3/8) in upper side and green (5GY 5/10 to 6/10) in lower side. Petal bases are free (not fused), petal color is white (10YR 8/1) at the base and deep purple (5RP 3/4 to 3/8) at the tip. Petals are imbricate. Flowers produce low number of pollen at the anthers and style is medium in length (same length as the stamens).

Fruit:

*I. General.*—After opening of the first flower, it takes 96±2 days for the 'Rosé' fruit to develop and ripe. Fruit has distinct aromatic and with medium content of fiber. The fruitlets are flat in the center and bulky in the borders.

*II. Fruit shape.*—The fruit shape is cylindrical. Its average weight is 1492±24 g with a length of 15.7±0.1 cm (crown not included), 12.8±0.1 cm of diameter at base, 12.1±0.1 cm of diameter at the middle portion and 11.4±0.1 cm of diameter at the upper part. It has a core diameter of 2.7±0.1 cm (Table 7).

*III. Fruit shell.*—Color is dark green (5G 5/6 to 5/10) until 3-4 weeks before maturity, and then the shell produces "Tiger" color (FIG. 5). The Tiger trait is defined as the color in shell has in the shoulder of each fruitlet a combination of colors green (5G 7/6 to 7/10), yellow (5Y 7/6 to 7/10), orange (5YR 3/5 to 6/5) and red (5R 2/4 to 5/4) due to expression of carotenoid genes in the shell (FIGS. 5-7). Fruit shell color at point of consume is yellow/orange (2.5Y 8/8 to 7.5YR 7/10, FIG. 6).

*IV. Peduncle.*—Fruit develops from the apical meristem of the plant on a short peduncle. At the fruit ripening stage, peduncle reaches a length of 17.0±0.3 cm and diameter of 2.5±0.3 cm (Table 7) and is green (5GY 4/6). Trichomes are present on peduncle. Imbricate bracts are present at the base of peduncle. The average length of the longest bract is 18.7±6.2 cm.

*V. Crown.*—The crown of 'Rosé' is conical in shape and similar to MD2 for weight and length (Table 9), and classified as long (>20 cm) and heavy (>130 g). Color of crown leaves is 5GY 6/4 to 8/4.

*VI. Flesh.*—The flesh is characterized by having a firmness of 3.4±0.1 g/N and succulence of 0.50±0.01 ml/g (Table 7). Fruit flesh is firm and fibrous with acidity, Brix degrees and pH similar to those of MD2 (Table 4), however, there are statistically significant differences between the two varieties for nutrients such as lycopene; β-carotene, vitamin C and potassium (see Table 5). The lycopene makes the flesh color light red (5R 7/6 to 7/8, 7.5R 7/6 to 7/8, 7.5R 6/6 to 6/8) with orange-yellow to golden yellow (2.5Y 8/8 to 8/10) spots. Number of spots can vary between 0 to 10 depending on the growing conditions. Minor differences between Rosé and MD2 flesh were noted in certain other nutrient components (ash, carbohydrates, moisture, sucrose, vitamin C, and leucine) (Table 6), however, these differences are within the reported range of nutrients in pineapple varieties and are considered to be biologically insignificant within the context of the American diet.

Plant/fruit resistance/susceptibility to pests and diseases: Resistance/susceptibility of Rosé to *Fusarium subglutinans* and other pests and diseases are expected to be same as MD2 (see Morales et al. 2006 U.S. Pat. No. 16,328 for MD2 traits).

Vegetative propagules: Commercial propagation is via vegetative propagules (suckers, stem shoots, hapa and slips and fruit crowns, FIG. 12). The 'Rosé' plant produces an average of 0.72±0.06 slips (Table 7), 0.76±0.02 ground suckers (low number), 0.90±0.13 suckers (low number), and 0.40±0.02 hapas (low number) (Table 8).

Vigor: It is considered that the plant vigor is similar to MD2.

Harvest: Under the Buenos Aires region, Costa Rica conditions, Plant crop is harvested 150-170 days after forcing depending on season (dry or rainy), Ratoon Crop is harvested 12 months after Plant Crop is harvested.

Storage: Storage and post-harvest characteristics of Rosé is expected to be same as MD2.

Yield: Estimated yield is same as MD2, 120-125 MT/ha in Plant Crop and 95-100 MT/ha in Ratoon Crop.

Market: Fruit will be designated to the international fruit market and commercialized into the fresh fruit market. Residual fruit (as defined in "DETAILED DESCRIPTION OF THE INVENTION" section) may be processed as juice or frozen product.

Tables: Tables 4-10 compare Rosé and MD2. Twenty-one quantitative characteristics measured in details for Rosé and MD2 showed that there are no statistically significant differences between the two varieties for the 21 characteristics (Table 7). Also, detailed phenotypes measured for Rosé and MD2 showed that among 17 traits only flesh color and shell color are significantly different in the two varieties (Table 8). Sensory analyses done for Rosé and MD2 fruits showed that there are no statistically significant differences between the two varieties for all 11 attribute measured (Table 9 and 10).

TABLE 1

Genetic Elements of plasmid pHCW1

| Genetic Element | Source and Function |
|---|---|
| RB | A 25 by nucleotide sequence that acts as the initial point of DNA transfer into plant cells which was originally sequenced from pTiA6 (Barker et al., 1983). |
| pVS1 | The pVS1 replicon derived from *Pseudomonas aeruginosa,* which ensures replication in *Agrobacterium tumefaciens* (Itoh et al., 1984). |
| TetRA | A tetracycline resistance gene from plasmid RP1, which allows for selection of the binary plasmid in *Agrobacterium tumefaciens* and*Escherichia coli* (Waters et al., 1983). |
| pACYC | The origin of replication from plasmid pACYC, which en sures replication in*Escherichia coli* (Chang et al., 1979). |
| LB | A 25-nucleotide sequence that delimits the T-DNA transfer and acts as the endpoint of DNA transfer into plant cells. It was originally isolated from TiA6 (Barker et al., 1983). |
| MCS | A 110-nucleotide sequence that synthetically was created, which is composing of multiple cloning restriction sites in order to allow integration of different cassettes into the plasmid. |

TABLE 2

Genetic Elements of T-DNA in plasmid pHCW.T-7 in AG76

| Genetic Element | Size (Kb) | Function (Reference) |
|---|---|---|
| BRIp2.5 | 2.5 | A promoter derived from the bromelain inhibitor (BRI) gene from *Ananas comosus* that drives fruit-enhanced expression of the target gene(s). |
| Psy | 1.131 | A phytoene synthase (Psy) gene from *Citrus reticulata,* identical to the gene isolated from mandarin fruit (Ikoma et al. 2001), which encodes an enzyme in carotenoid biosynthesis. |
| Ubpter | 0.94 | A terminator derived from the polyadenylation sequence of the ubiquitin (Ubi) gene from *Ananas comosus* terminates transcription of the transgene(s). |
| BRIp2.5 | 2.5 | A promoter derived from the promoter sequence from the bromelain inhibitor (BRI) gene from *Ananas comosus* that drives fruit-enhanced expression of the RNAi transgene. |
| eLyc sense fragment | 0.504 | A fragment of the lycopene g-cyclase gene from *Ananas comosus* in sense orientation, which is used in an RNAi expression system to down-regulate endogenous lycopene c-cyclase, an enzyme in carotenoid biosynthesis. |
| ST-LS1 | 0.193 | An intron of the light-inducible tissue-specific ST-LS1 gene from *Solanum tuberosum* that functions as a spacer between sense and antisense gene fragments enhancing vector stability. |
| eLyc antisense fragment | 0.504 | A fragment of the lycopene E-cyclase gene from *Ananas comosus* in antisense orientation, which is used in an RNAi expression system to down-regulate endogenous lycopene s-cyclase, an enzyme in carotenoid biosynthesis. |
| Ubpter | 0.94 | A terminator derived from the polyadenylation sequence of the ubiquitin (Ubi) gene from*Ananas comosus* terminates transcription of the RNAi transgene. |
| BRIp2.5 | 2.5 | A promoter derived from the promoter sequence from a bromelain inhibitor (BRI) gene from *Ananas comosus* that drives fruit-enhanced expression of the RNAi transgene. |
| b-Lyc sense fragment | 0.619 | A fragment of the lycopene 13-cyclase gene from *Ananas comosus* in sense orientation, which is used in an RNAi expression system to down-regulated endogenous lycopene 13-cyclase, an enzyme in carotenoid biosynthesis. |
| ST-LS1 | 0.193 | An intron of the light-inducible tissue-specific ST-LS1 gene from *Solanum tuberosum* (Eckes et al, 1986) that functions as a spacer between sense and antisense gene fragments enhancing vector stability. |
| b-Lyc antisense fragment | 0.619 | A fragment of the lycopene 13-cyclase gene from *Ananas comosus* in antisense orientation, which is used in an RNAi expression system to down-regulated endogenous lycopene 13- cyclase, an enzyme in carotenoid biosynthesis. |
| Ubpter | 0.94 | A terminator derived from the polyadenylation sequence of the ubiquitin (Ubip) gene from*Ananas comosus* terminates transcription of the RNAi transgene. |
| | | Selectable Marker |
| EHS1.7-Ubp1.5 | 4.257 | A promoter derived from the epoxide hydrolase (EHS) gene fused to the ubiquitin (Ubip) gene promoter and the native intron from *Ananas comosus* that drives constitutive expression of the selectable marker gene. |
| EHS1.7 | 1.7 | A promoter derived from the epoxide hydrolase (EHS) gene from *Ananas comosus* (Neuteboom et al, 2002) that drives constitutive expression of the selectable marker gene. |
| Ubp1.5 | 1.5 + 1.057 | A 1.5 kb tetrameric ubiquitin gene promoter from pineapple (*Ananas comosus*), which drives constitutive expression of the selectable marker gene. The promoter includes an endogenous 1057 by intron sequence. |
| ALS | 1.17 | A mutant acetolactate synthase gene from tobacco (*Nicotiana tabacum*), which confers resistance to chlorsulfuron and allows selection of transformed plant cells (Chaleff and Mauvais, 1984; Lee et al., 1988). |

TABLE 2-continued

Genetic Elements of T-DNA in plasmid pHCW.T-7 in AG76

| Genetic Element | Size (Kb) | Function (Reference) |
|---|---|---|
| ALS 3' | 2.7 | An endogenous terminator derived from untranslated polyadenylation signal of the acetolactate synthase (ALS) gene from *Nicotiana tabacum* (Chaleff and Mauvais, 1984; Lee et al., 1988). |

TABLE 3

Genetic Elements of T-DNA in plasmid pHCWflACC3'-2 in AG62. Elements are the same as above (Table 2) except those mentioned below.

| Genetic Element | Size (Kb) | Function (Reference) |
|---|---|---|
| flACS(+) sense | 0.406 | A 406 by 3' sequence of meristem-specific ACC synthase gene, isolated from pineapple (*A. comosus*, in the sense orientation, which is used in an RNAi expression system to down-regulate endogenous ACC synthase, a key enzyme in ethylene biosynthesis, thereby producing a plant that displays improved characteristics such as delayed flowering. |
| flACS(−) antisense | 0.406 | A 406 by 3' sequence of meristem-specific ACC synthase gene, isolated from pineapple (*A. comosus*), in the antisense orientation. |

TABLE 4

Internal quality traits measured for MD2 and Rosé.

| | MD2 | | | | Rosé | | | | P- |
|---|---|---|---|---|---|---|---|---|---|
| Trait | N | Mean | Range | SE | N | Mean | Range | SE | value |
| Ascorbic acid (mg/100 g) | 120 | 34.5 | 6.9-59.3 | 0.93 | 501 | 35.9 | 9.8-73.0 | 0.45 | 0.161 |
| Citric acid (mg/100 g) | 121 | 0.6 | 0.30-0.87 | 0.01 | 503 | 0.57 | 0.15-1.47 | 0.01 | 0.411 |
| °Brix (% w/w) | 121 | 14.0 | 9.2-16.7 | 0.11 | 492 | 13.8 | 10.5-19.0 | 0.05 | 0.052 |
| pH | 115 | 3.6 | 3.1-4.5 | 0.03 | 487 | 3.7 | 3.2-4.6 | 0.01 | 0.678 |

N = Number of fruits analyzed during 2009-2013. SE = Standard error. Student's t test was performed to compare the analytes. There was no significant differences at P +21 0.05 between the two varieties (P-values are larger than 0.05).
All data were analyzed using InfoStat-Statistical Software, version 2008 (National University of Cordoba, Argentina)

TABLE 5

Carotenoids, vitamin C, and potassium levels in MD2 and Rosé.

| Nutrient | MD2 | | | | Rosé | | | | P- |
|---|---|---|---|---|---|---|---|---|---|
| composition | N | Mean | Range | SE | N | Mean | Range | SE | value |
| Lycopene (ppm) | 18 | 0.0 | 0.0-0.0 | 0.0 | 18 | 21.3 | 14.3-32.9 | 0.9 | **<0.000** |
| β-carotene (IU/100 g) | 18 | 28.1 | 20.8-39.5 | 1.5 | 18 | 8.9 | 5.0*-32.8 | 1.9 | **<0.000** |
| Vitamin C (mg/100 g) | 18 | 46.8 | 36.0-55.8 | 1.4 | 18 | 40.3 | 28.3-56.2 | 1.8 | 0.008 |

TABLE 5-continued

Carotenoids, vitamin C, and potassium levels in MD2 and Rosé.

| Nutrient | MD2 | | | | Rosé | | | | P- |
|---|---|---|---|---|---|---|---|---|---|
| composition | N | Mean | Range | SE | N | Mean | Range | SE | value |
| Potassium (mg/100 g) | 18 | 129 | 117-142 | 1.7 | 18 | 156 | 101-204 | 6.6 | **0.0003** |

*Limits of detection (LOD) for β-and α-carotene were 10 IU/100 g, hence the β-carotene values for the samples below LOD were considered to be 5 IU/100 g (mean of 0 and 10). α-carotene was also measured in the fruits and the values were below LOD for all samples tested.

N = Number of fruits analyzed. SE = Standard error. Student's t test was performed to compare the analytes. Results significantly different at $p < 0.001$ are shown in bold.

All data were analyzed using InfoStat-Statistical Software, version 2008 (National University of Cordoba, Argentina)

TABLE 6

Proximates, sugars, and amino acid levels in MD2 and Rosé

| | MD2 | | | |
|---|---|---|---|---|
| Analyte | N | Mean | Range | SE |
| Proximates | | | | |
| Total dietary fiber (%) | 18 | 2.8 | 1.9-3.3 | 0.11 |
| Ash (%) | 18 | 0.27 | 0.23-0.32 | 0.01 |
| Carbohydrates (%) | 18 | 12.0 | 10.1-13.4 | 0.18 |
| Fat (%) | 18 | 0.22 | 0.14-0.31 | 0.01 |
| Moisture (%) | 18 | 86.9 | 85.5-88.8 | 0.18 |
| Protein (%) | 18 | 0.58 | 0.37-0.73 | 0.02 |
| Sugars | | | | |
| Sucrose (%) | 18 | 4.26 | 3.54-5.08 | 0.11 |
| Fructose (%) | 18 | 2.34 | 1.59-3.12 | 0.09 |
| Glucose (%) | 18 | 2.00 | 1.33-2.74 | 0.08 |
| Amino acids | | | | |
| Leucine (%) | 18 | 0.034 | 0.020-0.051 | 0.002 |
| Isoleucine (%) | 18 | 0.025 | 0.010-0.040 | 0.002 |
| Methionine (%) | 18 | 0.016 | 0.004-0.044 | 0.003 |
| Valine (%) | 18 | 0.031 | 0.023-0.049 | 0.002 |

| | Rosé | | | | P- |
|---|---|---|---|---|---|
| Analyte | N | Mean | Range | SE | value |
| Proximates | | | | | |
| Total dietary fiber (%) | 18 | 2.9 | 1.7-3.8 | 0.15 | 0.509 |
| Ash (%) | 18 | 0.31 | 0.20-0.42 | 0.01 | 0.001 |
| Carbohydrates (%) | 18 | 11.2 | 10.0-12.7 | 0.18 | 0.002 |
| Fat (%) | 18 | 0.17 | 0.10-0.25 | 0.01 | 0.016 |
| Moisture (%) | 18 | 87.8 | 86.5-89.0 | 0.18 | 0.002 |
| Protein (%) | 18 | 0.54 | 0.35-0.78 | 0.03 | 0.370 |
| Sugars | | | | | |
| Sucrose (%) | 18 | 3.81 | 3.09-4.50 | 0.09 | 0.004 |
| Fructose (%) | 18 | 2.07 | 1.51-2.68 | 0.07 | 0.026 |
| Glucose (%) | 18 | 1.80 | 1.26-2.47 | 0.06 | 0.063 |
| Amino acids | | | | | |
| Leucine (%) | 18 | 0.026 | 0.017-0.040 | 0.002 | 0.004 |
| Isoleucine (%) | 18 | 0.029 | 0.012-0.041 | 0.002 | 0.240 |
| Methionine (%) | 18 | 0.008 | 0.004-0.012 | 0.001 | 0.011 |
| Valine (%) | 18 | 0.033 | 0.018-0.049 | 0.002 | 0.399 |

N = Number of fruits analyzed. SE = Standard error. Nutrient levels are shown in % FW. Student's t test was performed to compare the analytes. Results significantly different at $P < 0.01$ are shown in bold.
All data were analyzed using InfoStat-Statistical Software, version 2008 (National University of Cordoba, Argentina)

TABLE 7

Quantitative characteristics measured for Rosé and MD2

| Characteristics | MD2 N | Mean | Range | SE |
|---|---|---|---|---|
| Pre-forcing stage | | | | |
| Growth rate* (mm/day) | 75 | 1.78 | 1.18-2.27 | 0.02 |
| Forcing stage | | | | |
| Plant height (cm) | 75 | 118 | 84-142 | 1 |
| D leaf length at forcing (cm) | 75 | 98.1 | 73-117 | 2.8 |
| Anthesis stage | | | | |
| Stem height (cm) | 74 | 33.3 | 25-47 | 0.5 |
| No. of flowers/inflorescence | 52 | 90.5 | 70-136 | 1.8 |
| Harvest stage | | | | |
| Peduncle length (cm) | 75 | 16.8 | 10-23 | 0.3 |
| Peduncle diameter (cm) | 75 | 2.49 | 1.6-3.4 | 0.04 |
| Fruit weight (g) | 74 | 1559 | 876-2425 | 36 |
| Fruit length (cm) | 74 | 15.1 | 11.0-19.8 | 0.2 |
| Fruit diameter at base (cm) | 74 | 12.3 | 10.1-14.0 | 0.1 |
| Fruit diameter at the middle portion (cm) | 74 | 12,3 | 11.0-14.0 | 0.1 |
| Fruit diameter at the tip (cm) | 74 | 11.5 | 9.8-13.3 | 0.1 |
| Flesh firmness** (g/Newton) | 72 | 3.48 | 1.2-5.8 | 0.1 |
| Flesh succulence (ml juice/g FW) | 72 | 0.46 | 0.26-0.86 | 0.01 |
| Core diameter (cm) | 73 | 2.47 | 1.5-3.2 | 0.18 |
| Fruit °Brix | 72 | 15 | 7.0-9.0 | 0.16 |
| Citric acid (mg/100 g) | 71 | 0.48 | 0.22-0.77 | 0.01 |
| Vitamin C (mg/100g) | 71 | 34.7 | 9.6-67.7 | 1,5 |
| Sugar/acid ratio | 70 | 34.2 | 17.4-65.1 | 1.3 |
| Juice pH | 61 | 3.7 | 3.0-4.3 | 0.03 |
| Shoot development stage | | | | |
| No. of slips | 75 | 0.84 | 0-3 | 0.08 |

| Characteristics | Rosé N | Mean | Range | SE | P-value |
|---|---|---|---|---|---|
| Pre-forcing stage | | | | | |
| Growth rate* (mm/day) | 150 | 1.72 | 1.15-2.31 | 0.02 | 0.074 |
| Forcing stage | | | | | |
| Plant height (cm) | 150 | 116 | 84-150 | 1 | 0.272 |
| D leaf length at forcing (cm) | 150 | 97.6 | 62-123 | 2.0 | 0.881 |
| Anthesis stage | | | | | |
| Stem height (cm) | 74 | 34.7 | 27-42 | 0.45 | 0.023 |
| No. of flowers/inflorescence | 111 | 90.8 | 64-134 | 1.2 | 0.891 |
| Harvest stage | | | | | |
| Peduncle length (cm) | 75 | 17.0 | 12-22 | 0.3 | 0.547 |
| Peduncle diameter (cm) | 150 | 2.50 | 1.2-3.3 | 0.03 | 0.922 |
| Fruit weight (g) | 225 | 1492 | 699-2308 | 24 | 0.110 |
| Fruit length (cm) | 225 | 15.7 | 10.3-18.0 | 0.1 | 0.083 |
| Fruit diameter at base (cm) | 225 | 12.8 | 9.5-14.5 | 0.1 | 0.127 |
| Fruit diameter at the middle portion (cm) | 225 | 12.1 | 10.0-14.5 | 0.1 | 0.127 |

TABLE 7-continued

Quantitative characteristics measured for Rosé and MD2

| | | | | | |
|---|---|---|---|---|---|
| Fruit diameter at the tip (cm) | 225 | 11.4 | 8.5-13.0 | 0.1 | 0.398 |
| Flesh firmness** (g/Newton) | 221 | 3.40 | 1.8-6.8 | 0.1 | 0.500 |
| Flesh succulence (ml juice/g FW) | 219 | 0.48 | 0.21-1.12 | 0.01 | 0.207 |
| Core diameter (cm) | 219 | 2.68 | 1.5-3.6 | 0.11 | 0.328 |
| Fruit °Brix | 212 | 15 | 12.2-18.0 | 0.10 | 0.731 |
| Citric acid (mg/100 g) | 192 | 0.49 | 0.22-0.80 | 0.01 | 0.789 |
| Vitamin C (mg/100g) | 63 | 35.2 | 14.7-76.6 | 1.6 | 0.801 |
| Sugar/acid ratio | 189 | 33.8 | 17.9-73.2 | 0.8 | 0.767 |
| Juice pH | 53 | 3.6 | 3.0-3.9 | 0.03 | 0.244 |
| Shoot development stage | | | | | |
| No. of slips | 150 | 0.72 | 0-3 | 0.06 | 0.223 |

*Growth rate was measured by height of plant at forcing (mm)-height of plant at planting (mm)/number of days from planting to forcing.
**Flesh firmness was measured by penetrometer.

Tukey's hsd was used for statistical analyses. N = Number of fruits or plants analyzed. SE = Standard error. Results show that there is no significant differences between the two varieties at $P < 0.01$.

TABLE 8

Phenotypes measured for Rosé and MD2 based on the Brazilian descriptors (MALFSB, 2003) and Corporacion de Desarrollo Agricola Del Monte measurements for pineapple.

| Characteristics | MD2 N | 1 | 2 | 3 |
|---|---|---|---|---|
| Color of petals | 75 | 100.0% Purple | 0.0% White | |
| Homogeneity of shell | 74 | 100.0% Yes | 0.0% No | |
| Relief (surface) of fruitlet | 74 | 100.0% Flat | 0.0% Prominent | 0.0% Highly prominent |
| Fruit aroma | 71 | 14.1% Weak | 66.2% Medium | 19.7% Strong |
| Fruit fibemess | 71 | 2.82% Low | 54.90% Medium | 42.20% High |
| Fruit shape | 74 | 0.00% Conic | 21.60% Conic to cylindric | 71.60% Cylindric |
| Flesh color uniformity | 74 | 100% Yellow | 0.0% ⅓ pink | 0.0% ⅔ pink |
| Flesh color intensity | 74 | 100% Golden yellow | 0.0% Pale pink | 0.0% Pink |
| Tiger pattern (shell color) | 75 | 0.0% Yes | 100.0% No | |
| Crown position | 74 | 29.70% Erect | 60.80% Open | 9.46% Decumbent |
| Crown length (cm) | 72 | 8.30% Short | 20.80% Medium | 70.80% Long |
| Crown weight (g) | 71 | 1.40% Low | 2.80% Medium | 95.80% High |
| No. of active leaves | 75 | 100 0% Low | 0.0% Medium | 0.0% High |
| No. of hapas (ratoon) | 75 | 100.0% Low | 0.0% Medium | 0.0% High |
| No. of ground suckers | 74 | 100.0% Low | 0.0% Medium | 0.0% High |
| Spines | 74 | 100.0% Absent | 0.0% Inconspicuous | 0.0% Conspicuous |
| Distribution of spines at leaf margin | 74 | 0.0% At base only | 100.0% At apex only | 0.0% At base and apex |

TABLE 8-continued

Phenotypes measured for Rosé and MD2 based on the Brazilian descriptors (MALFSB, 2003) and Corporacion de Desarrollo Agricola Del Monte measurements for pineapple.

| | MD2 | | Rosé | |
|---|---|---|---|---|
| Characteristics | 4 | 5 | N | 1 |
| Color of petals | | | 150 | 100.0% Purple |
| Homogeneity of shell | | | 225 | 100.0% Yes |
| Relief (surface) of fruitlet | | | 221 | 100.0% Flat |
| Fruit aroma | | | 220 | 6.36% Weak |
| Fruit fibemess | | | 218 | 5.05% Low |
| Fruit shape | 6.76% Elliptic | 0.00% Global | 149 | 0.00% Conic |
| Flesh color uniformity | 0.0% Full pink | | 210 | 0.00% Yellow |
| Flesh color intensity | 0.0% Pink/Red | | 162 | 0.00% Golden |
| Tiger pattern (shell color) | | | 225 | 100.0% Yes |
| Crown position | | | 225 | 26.60% Erect |
| Crown length (cm) | | | 147 | 22.50% Short |
| Crown weight (g) | | | 139 | 15.30% Low |
| No. of active leaves | | | 225 | 100.0% Low |
| No. of hapas (ratoon) | | | 225 | 100.0% Low |
| No. of ground suckers | | | 225 | 100.0% Low |
| Spines | | | 225 | 100.0% Absent |
| Distribution of spines at leaf margin | 0.0 % Regular | 0.0% Irregular | 225 | 0.0% At base only |

| | Rosé | | | | P- |
|---|---|---|---|---|---|
| Characteristics | 2 | 3 | 4 | 5 | value* |
| Color of petals | 0.0% White | | | | >0.9999 |
| Homogeneity of shell | 0.0% No | | | | >0.9999 |
| Relief (surface) of fruitlet | 0.0% Pro-minent | 0.0% Highly prominent | | | >0.9999 |
| Fruit aroma | 66.80% Medium | 26.80% Strong | | | 0.084 |
| Fruit fibemess | 64.20% Medium | 30.70% High | | | 0.178 |
| Fruit shape | 15.40% Conic to cylindric | 69.80% Cylindric | 14.70% Elliptic | 0.00% Global | 0.155 |
| Flesh color uniformity | 8.60% ⅓ pink | 3.30% ⅔ pink | 88.10% Full pink | | **<0.0001** |
| Flesh color intensity | 1.23% Pale pink yellow | 35.19% Pink | 63.60% Pink/Red | | **<0.0001** |
| Tiger pattern (shell color) | 0.0% No | | | | **<0.0001** |
| Crown position | 59.50% Open | 13.70% De-cumbent | | | 0.6 |
| Crown length (cm) | 22.50% Medium | 55.10% Long | | | 0.024 |

TABLE 8-continued

Phenotypes measured for Rosé and MD2 based on the Brazilian descriptors (MALFSB, 2003) and Corporacion de Desarrollo Agricola Del Monte measurements for pineapple.

| | | | | | |
|---|---|---|---|---|---|
| Crown weight (g) | 2.80% Medium | 81.90% High | | | 0.011 |
| No. of active leaves | 0.0% Medium | 0.0% High | | | >0.9999 |
| No. of hapas (ratoon) | 0.0% Medium | 0.0% High | | | >0.9999 |
| No. of ground suckers | 0.0% Medium | 0.0% High | | | >0.9999 |
| Spines | 0.0% Incon-spicuous | 100.0% Con-spicuous | | | >0.9999 |
| Distribution of spines at leaf margin | 100.0% At apex only | 0.0% At base and apex | 0.0% Regular | 0.0% Ir-regular | >0.9999 |

A contingency table was created to make a distribution and Chi-square was used for statistical analyses. N = Number of plants or fruits analyzed.
Results show no biologically significant differences between the two varieties ($P < 0.01$) with the exception of fruit color traits (P values in bold).

TABLE 9

Sensory analyses of Rosé and MD2 fruits.

| Sensory | MD2 | | | |
|---|---|---|---|---|
| characteristic | N | 1 | 2 | 3 |
| Aroma | 27 | 33.33% (Highly aromatic) | 57.14% (Aromatic) | 9.52% (Slightly aromatic) |
| Taste | 27 | 37.11% (Excellent) | 52.58% (Good) | 10.31% (Indifferent) |
| Sweetness | 27 | 39.13% (High) | 57.97% (Normal) | 2.90% (Low) |
| Acidity | 27 | 6.98% (High) | 46.51% (Normal) | 46.51% (Low) |
| Other flavors (Bitter, Salty, Other) | 27 | 0.00% High | 9.38% (Moderate) | 90.63% (None) |
| After taste | 27 | 5.17% (Very high sense) | 86.21% (Slight sense) | 8. 62% (None ) |
| Juiciness | 27 | 55.26% (High) | 44.74% (Normal) | 0.00% (Low) |
| Fiberness | 27 | 25.00% (High) | 63.33% (Normal) | 11.67% (Low) |
| Consistency | 27 | 30.16% (Firm) | 69.84% (Normal) | 0.00% (Soft) |
| Visual appearance of fresh cuts | 27 | 33.68% (Liked very much) | 53.68% (Acceptable) | 12.63% (Indifferent) |

| Sensory | MD2 | | Rosé | |
|---|---|---|---|---|
| characteristic | 4 | N | 1 | 2 |
| Aroma | N/A | 27 | 20.00% (Highly aromatic) | 70. 00% (Aromatic) |
| Taste | 0.00% (Bad) | 27 | 4.65% (Excellent) | 80.23% (Good) |
| Sweetness | N/A | 27 | 16.07% (High) | 67.86% (Normal) |
| Acidity | N/A | 27 | 12.77% (High) | 51.06% (Normal) |
| Other flavors (Bitter, Salty, Other) | N/A | 27 | 3.23% (High) | 9.68% (Moderate) |
| After taste | N/A | 27 | 0.00% (Very high sense) | 80.77% (Slight sense) |
| Juiciness | N/A | 27 | 27.27% (High) | 69.70% (Normal) |

TABLE 9-continued

| | | | | |
|---|---|---|---|---|
| Fiberness | N/A | 27 | 16.67% (High) | 62.67% (Normal) |
| Consistency | N/A | 27 | 34.38% (Firm) | 65.63% (Normal) |
| Visual appearance of fresh cuts | N/A | 27 | 43.56% (Liked very much) | 50.508% (Acceptable) |

| Sensory characteristic | Rosé 3 | Rosé 4 | P-value |
|---|---|---|---|
| Aroma | 10.00% (Slightly aromatic) | N/A | 0.683 |
| Taste | 13.95% (Indifferent) | 1.16% (Bad) | 0.063 |
| Sweetness | 16.07% (Low) | N/A | 0.052 |
| Acidity | 36.17% (Low) | N/A | 0.833 |

TABLE 9-continued

| | | | |
|---|---|---|---|
| Other flavors (Bitter, Salty, Other) | 87.10% ( None) | N/A | 0.284 |
| After taste | 19.23% (None) | N/A | 0.062 |
| Juiciness | 3.03% (Low) | N/A | 0.051 |
| Fiberness | 20.37% (Low) | N/A | 0.314 |
| Consistency | 0.00% (Soft) | N/A | >0.9999 |
| Visual appearance of fresh cuts | 5.94% (Indifferent) | N/A | 0.465 |

Twenty-seven fruits each of Event EF2-114 and MD2 were tested by 13 trained panelists. A Chi-square test was performed for the analyses of qualitative data collected. There were no statistically significant differences ($P < 0.05$) between the two varieties for sensory attributes.

What is claimed is:

1. A new and distinct variety of pineapple plant named 'Rosé' as illustrated and described herein.

* * * * *

Sunny side

Shady side